(12) United States Patent
Hanna (10) Patent No.: US 9,533,085 B2
(45) Date of Patent: Jan. 3, 2017

(54) INTRACARDIAC IMPLANT—TOTAL ARTIFICIAL HEART

(76) Inventor: Ihab Daoud Hanna, Cairo (EG)

(*) Notice: Subject to any disclaimer, the term of this patent is extended or adjusted under 35 U.S.C. 154(b) by 418 days.

(21) Appl. No.: 13/060,701

(22) PCT Filed: Feb. 19, 2009

(86) PCT No.: PCT/EG2009/000006
§ 371 (c)(1),
(2), (4) Date: Feb. 25, 2011

(87) PCT Pub. No.: WO2010/078873
PCT Pub. Date: Jul. 15, 2010

(65) Prior Publication Data
US 2011/0153010 A1 Jun. 23, 2011

(30) Foreign Application Priority Data
Jan. 8, 2009 (EG) .................. 2009010031

(51) Int. Cl.
*A61M 1/10* (2006.01)
*A61M 1/12* (2006.01)

(52) U.S. Cl.
CPC .......... *A61M 1/1053* (2013.01); *A61M 1/106* (2013.01); *A61M 1/1068* (2013.01); *A61M 1/12* (2013.01)

(58) Field of Classification Search
CPC ............................................ A61M 1/10
USPC ........................................ 623/3.11
See application file for complete search history.

(56) References Cited

U.S. PATENT DOCUMENTS 5,139,517 A 8/1992 Corral
2008/0045777 A1* 2/2008 Jassawalla .......... A61M 1/1053
600/16

* cited by examiner

*Primary Examiner* — Matthew Schall
(74) *Attorney, Agent, or Firm* — Seth L. Hudson; Clements Bernard PLLC (57) ABSTRACT

The present invention provides methods and systems for a biomaterial medical implant device for treating patients with HF and/or intractable dyrhythmia. It either is implanted inside the cardiac cavity(ies), ICI, or after their removal, TAH.

The embodiment consists of 2 layers. Layer 1 (16) is immobile and adherent to the basement. Layer 2 (17) reflects from layer 1 and faces the cavity. Layer 2 moves inwards (systole) and backwards (diastole) by between-layers Concertina-like elastic fibers and/or a spring (22), on-surface diagonally crossing elastic fibers (27), or sheets (29&30) of electromagnetic coils (34), that are adherent to both layers from the inside. Layer 2 moves through the electromagnetic coil causing its attraction to layer 1, when polarities are different and repulsion when polarities are similar.

18 Claims, 8 Drawing Sheets

INTRACARDIAC IMPLANT—TOTAL ARTIFICIAL HEART

FIELD OF THE INVENTION

The present invention relates to a medical invention in the field of heart diseases, and more generally relates to a medical implant designed to be surgically implanted intracardiac (ICI) or extracardiac (TAH) for the aim of permanently treating heart failure patients and it can be used to treat patients with intractable serious ventricular dysrhythmias whether isolated or in the course of heart failure.

BACKGROUND OF THE INVENTION

The currently available methods to treat heart failure are numerous. However they present less hope to survival and quality of life than expected. Among the newest tools in fighting heart failure there stands stem cell therapy. Stem Cell Therapy aims at the rejuvenation of the inactive weak cardiac muscle cells through the introduction of stem cells which are capable of homing, resynthesis of and replacing myocardial cells. Stem cell therapy has proved limited success with concerns about the safety and prognosis.

Another relatively recent method is cardiac resynchronisation therapy 'CRT'. This entails the introduction of a third lead in a position behind the left ventricle where it can be paced. Through this timed event, the intraventricular as well as the interventricular dyssynchrony may be corrected. This mode of treatment has proved effective in increasing the 6-min walk test and patient symptoms and signs. CRT still poses questionable results and benefits. Also choosing the candidate with potential future success has many limitations as well.

Cardiac transplantation is a more solid treatment option of adding somebody's heart to replace another heart, a human heart from a dead donor to a heart failure recipient. There are a wealth of difficulties to the donor and recipient. Difficulties to the donor include a rarity of donor's hearts which is <3000/year worldwide, heart preservation, transportation, laboratory tests, intrinsic heart disease, ABO blood type compatibility, Donor-Recipient size disparity, transmissible diseases, a 2-5 fold mortality risk to recipient with higher donor age, coronary artery disease, allograft rejection, allograft vasculopathy, and transplanted organ rejection (4%/year).

Difficulties to the recipient include immunosuppressive and cytotoxic medications that lead to malignancy and multi system organ failure, right ventricular (RV) failure, and absence of chronotropic response with the dennervated transplanted heart.

Most patients awaiting a heart transplant are awarded a pretransplant procedure; a ventricular assist device 'VAD'. They are either short-term, or long-term, i) Pulsatile; or ii) Non-Pulsatile.

They are temporarily placed and lasting in proper function from few months to a maximum of 3 years. Infection is common due to the extracorporeal nature of cable connections, drive lines, console-controllers, . . . etc. Some require adequate intrathoracic space to accommodate; (needs BSA>1.7 m2). Pulsatile devices need inflow and outflow valves. An inadequate cardiac output (COP), approximately 4-6 L/min, which does not permit physiological augmentation of COP with exercise. This method introduced abnormal metabolic and neurohumoral changes with the non-pulsatile devices due to the continuous nature of organ perfusion. All devices are pump-operated through inflow and outflow catheters. This pump operation will not solve any cardiac serious dysrhythmias; a common event in such terminal patients. Pump problems may include diaphragm rupture in 35% at 2 years.

Lastly, two common shared difficulties to both VAD's and heart transplantation have been clearer; both can help systolic dysfunction, but not diastolic dysfunction or diastolic heart failure. Both are helpless when cardiac dysrhythmias (Brady-, or Tachycardia) occur. They are unable to deliver DC shock, defibrillate or pace the slowing heart.

In developed countries, around 1-2% of adults suffer from heart failure, with an estimated annual mortality of approximately 21% in men and 17% in women. In the USA there are more than 5 million patients under treatment from congestive heart failure, with an estimated 550,000.00 new cases occur each year. Approximately one-half of the patients have moderately to severely reduced left ventricle (LV) systolic function. Approximately, these patients will need more than medical control to gain a better quality of life. The figure waiting for artificial hearts &/or cardiac transplantation is very huge.

The ICI-TAH embodiment targets patients with diseased heart muscle. Not only those with systolic failure who benefit from this embodiment, but patients with diastolic failure as well. Therefore, it targets the patient with right ventricular (RV) and/or LV Dilated-, Restrictive, and/or Hypertrophic Cardiomyopathy as well as other patients with serious pathology (e.g. native or prosthetic valvar pathology, septal defects, aneurysmal chamber dilatation, CABG-difficult patients) associated with heart failure. Patients as well with primary cardiac tumors will benefit from the embodiment. Also patients with critical intractable supraventricular or ventricular dysrhythmia, originating from whatever chamber, whether isolated or in the course of cardiomyopathy, will be candidates for the embodiment. Finally, installation includes; a stepped approach. First through surgical implantation by means of open heart surgery, with a second, more advanced, step of percutaneous catheter implantation that follows, when "ICI" is planned. A step, through transapical installation is another option.

BRIEF SUMMARY OF THE INVENTION

The biomaterial-made ICI and/or TAH embodiment is targeting the patient with heart failure and/or intractable dysrhythmia. The ICI embodiment is to be implanted inside the cardiac cavity(ies), with the option of removing all inner chamber structures and implanting an artificial valve, a surrogate valve (vis infra) or keeping the atrioventricular valve and apparatus. The TAH embodiment is replacing the diseased removed chambers. The embodiment can thus be implanted in one or more units according to the demand of each patient's diseased cardiac status. The TAH embodiment is connected to the existing cardiac outgoing and incoming vessels and stabilized in place to and within the thoracic cage by means of optional cords and/or threads which back up the basement of the embodiment, illustrated as layer 1 (16).

The TAH embodiment in the coming text has all the applications of the ICI embodiment with the following differences that do not apply to the TAH embodiment: no percutaneous application (i.e. no space to terminate in, when using the vascular route); no patchy application (i.e. no native heart tissue to implant on); and no DC shock/Defibrillation facility (i.e. no intervening heart tissue to deliver the shock).

When a chamber is nominated in the context of ICI embodiment, it implies its position in the TAH embodiment, for example when left ventricle 'LV' (4) is mentioned with the ICI embodiment, the corresponding term is still LV but only its position is implied because the LV in itself is removed and replaced with the TAH unit in the LV position. The same applies when mentioning interatrial or interventricular septum where the TAH embodiment septum will mean the embodiment artificial wall.

Each embodiment unit consists of 2 layers. Layer 1 (16), immobile and adherent to the endocardium (when ICI) or optional stabilizing cords (when TAH). Layer 2 (17) reflects from layer 1 and faces the cavity. Layer 2 moves inwards (systole) and backwards (diastole) by one or a combination of the following: i) Concertina-like elastic fibers and/or spring (22), ii) crossing diagonal elastic fibers (27) with or without simple node(s) 'SN' (28) or electromagnetic node(s) 'EMN' (28) that cross diagonally from one surface to the opposing, and/or iii) Sheets made of electromagnetic 'EM' coil(s) (29 and 30). These sheets are adherent to the inside of layers 1 and 2.

The mechanism of separation (systole) and attraction (diastole) of layers 1 and 2, is pulsatile and is through electromagnetic coils (34) which obey the law of attraction between different polarities and repulsion between similar polarities. All parts of the embodiment are shielded and insulated to guard against electromagnetic field dispersion into the surrounding media.

A battery/programmer/pacer/DC shock/defibrillator (21), (referred to as 'battery' in the whole text), feeds the embodiment through one or more cable leads emerging from the battery, and relay in one or point of entry onto the desired unit(s). The battery is infraclavicularly implanted or between both layers, externally or internally rechargeable through thermocouple technology.

Hemodynamic data information from the circulation, heart and body dynamics as well as battery programmable parameters are transmitted between the embodiment and the battery through one or more cables leads (13,14, and 20) as mentioned above.

Each embodiment connects internally through a network of fine cables between its both layers, with many electrodes (18) that serve as sensors, relay stations and booster to signal and power. The electrodes intermittently lie along the course of these fine cables. Each embodiment unit connects to its neighboring one, through bridging cables (19); either horizontal; when side-by-side units (1 and 2//3 and 4) or vertical; when longitudinal units (1 and 3//2 and 4).

The embodiment paces in single chamber and up to quadrichamber mode. Also a defib/DC shock facility when ICI. All programmable features will control systole and diastole as regards rate (r), power (p), duration (d) and distance of movement (d) ("collectively referred to as "ddrp") according to the sensed hemodynamics Unlike pacemakers which allow rate response only to native heart tissue, the embodiment allows "ddrp" response to an authentic guaranteed-response non-native tissue.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

Figure 1:
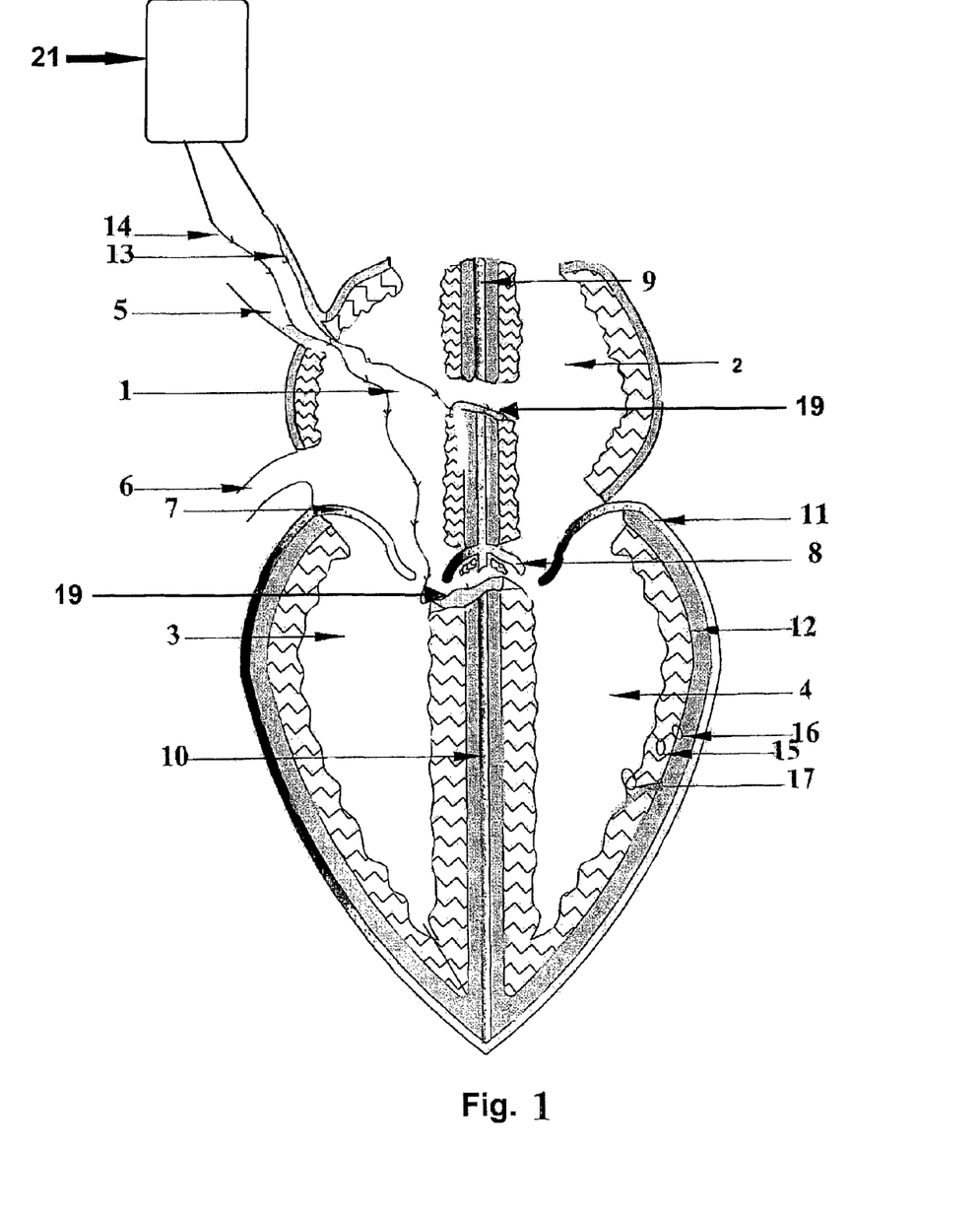
FIG. 1 is a schematic diagram for an intra cardiac plant (ICI) and the application sites and connections with preservation of the inner structures of the application chamber.

Referring now specifically to the drawings, and specifically to the medical implant of the present invention as illustrated in FIG. 1, the body (15) is formed of 2 layers consisting of layer 1 (16) and layer 2 (17). Layer 1 (16) rests on the cardiac endocardium (when ICI but not when TAH) (12). Layer 2 (17) reflects from layer 1 and faces the cardiac cavity (when ICI) or the replaced chamber (when TAH) from inside; right atrium (1), left atrium (2), right ventricle (3) or left ventricle (4), or a combination of more than one. The cardiac epicardium (11) is free from any attachments. The interatrial septum (9) permits a connecting bridging cable (19) to single station and the interventricular septum (10) also permits a connecting bridging cable (19) to a single station; both to LA (2) and LV (4) units respectively. These cables permit the left-sided embodiment to connect to the battery (21) with or without right-sided embodiment implantation. A separate cable lead (13) from the battery (21) supplies the right atrium (RA) (1) and/or the left atrium (LA) (2) units. Another separate cable lead (14) from the battery (21) supplies the RV (3) and/or the LV (4) units. Both cable leads (13 and 14) reach the heart through the superior vena cava (5) while the inferior vena cava (6) holds none. Looking at the internal attachment; the "ICI" embodiment can be attached to the "whole" inner chamber cavity, with preservation of the inner structures. The traction and release offered by the device movement to the ventricular myocardium will spontaneously initiate opening and closure of the mitral valve (8), through pressure gradient, thus permitting normal mitral diastolic properties.

Figure 2:
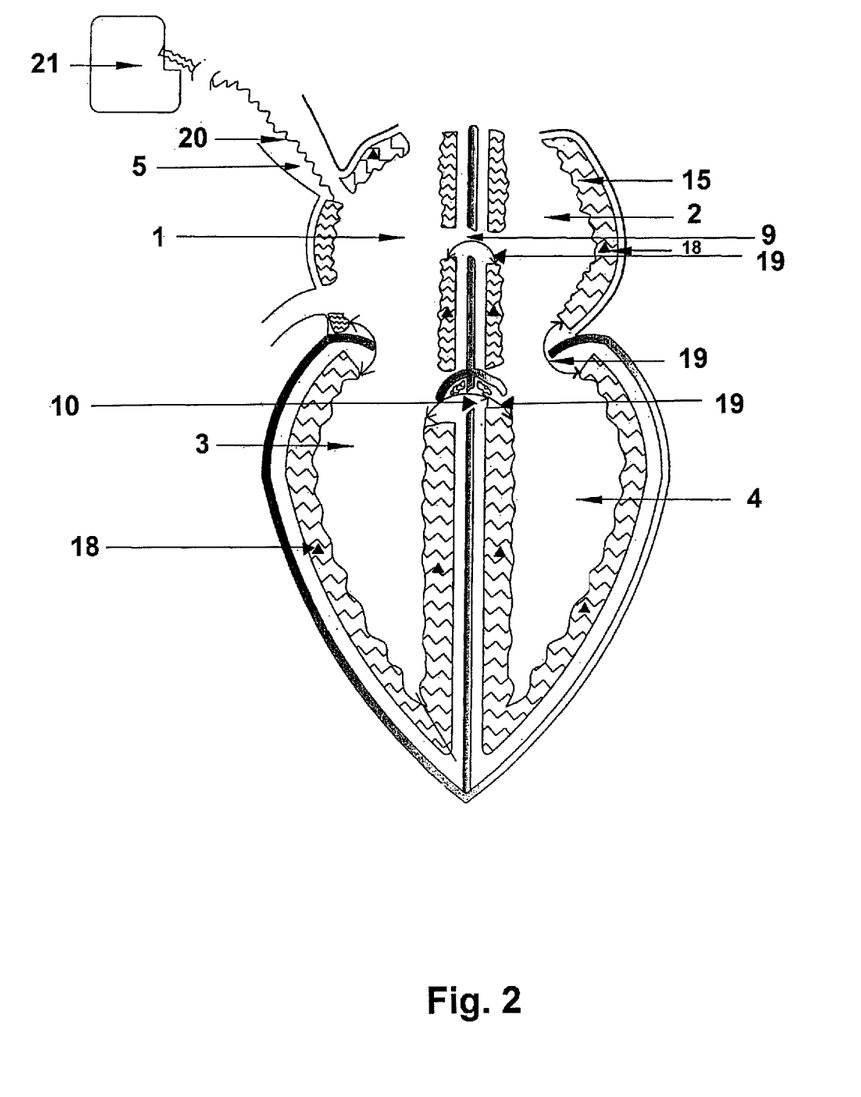
FIG. 2 is a schematic diagram of the ICI-TAH embodiment of the present invention using built-in electrodes, fine cable connections to all chambers.

One embodiment of the present invention is illustrated in FIG. 2 connects to all units through a single cable lead (20) connecting the battery (21) to a single station electrode (18) in RA unit (1). This cable lead (20) leaves the Battery/programmer/pacer/DC shock/defibrillator (21) to the SVC (5) where it terminates in RA unit electrode(s) (18). From this electrode(s) (18), data is interchanged between the embodiment and the Battery/programmer/pacer/DC shock/defibrillator (21), as well as power supply source. These electrodes (18) interchange data as well with other cardiac chamber units through bridging cables (19) that cross from one chamber unit to another. Bridging cables (19) cross from RA unit (1) to LA unit (2) through interatrial septostomy (9) and from RV unit (3) to LV unit (4) through interventricular septostomy (10) all at single point in each location. Electrodes (18) serve as hemodynamic and static/dynamic sensors, relay and booster stations: to data in both directions, and power source.

Figure 3:
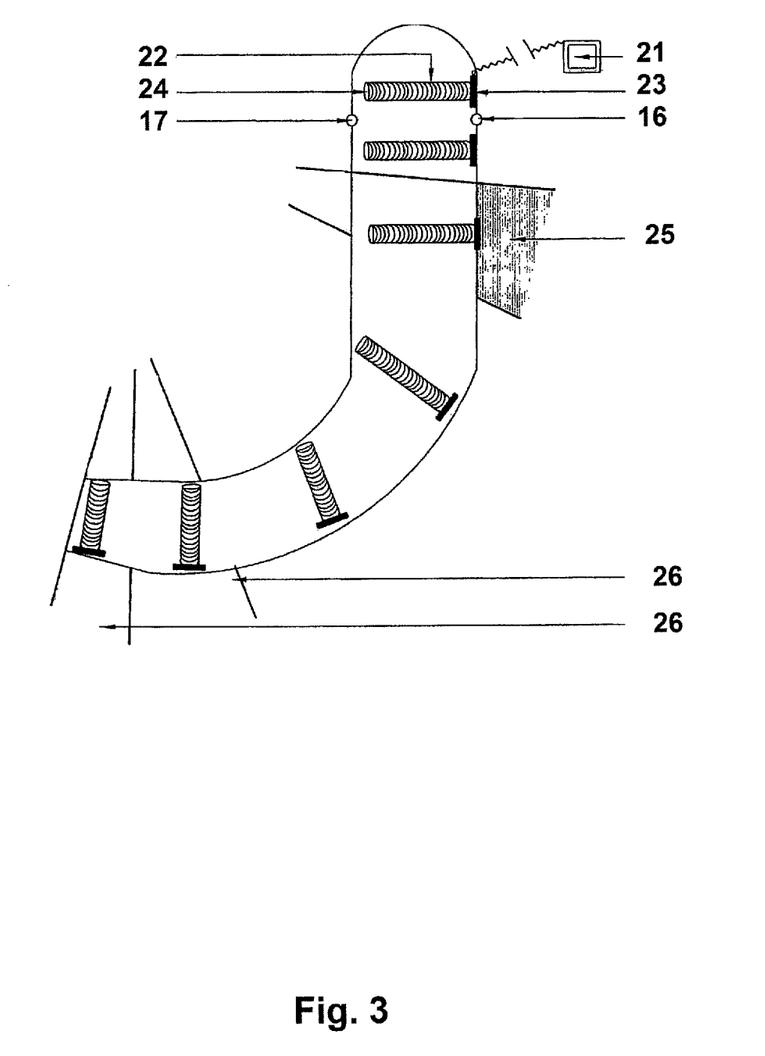
FIG. 3 is a perspective view of a longitudinal spring or elastic fibers in a concertina manner.

As shown in FIG. 3, elastic fibers and/or spring 'concertina' (22) attach to layer 1 (16) from one end (23) and to layer 2 (17) from the other end (24). The end (23) of concertina (22) lying on layer 1 (16) connects to the Battery/programmer/pacer/DC shock/defibrillator (21) and the other free end (24) compresses and springs out. The spring out (25) expresses the cardiac contraction in systole, while the compression of the concertina (26) expresses cardiac diastole. Both can be to variable programmable distances. Each elastic fiber or spring (22), contains several connected operating parts from inside. These parts are elastic element (reference numeral 33 in FIG. 8), electromagnetic coil (reference numeral 34 in FIG. 8), ferromagnetic core (reference numeral 35 in FIG. 8) and spring (reference numeral 36 in FIG. 8) shown and explained in FIG. 8. The EE, EMC & FMC can be arranged in several layers of sheets (not shown) instead of spanning the distance between layers 1 and 2 in a single application. This multilayered-sheets with the EM application upon, has the advantage of providing an integrated force with less EM field dispersion into the surrounding media.

The medical implant is composed of 2 layers, in a manner similar to that of the pericardiac sac, i—Layer 1—is the basement that faces the endocardium and is stabilized in place through one, all or combination of the following suggested techniques: Suturing it to the underlying base, biological glue, anchoring by hooks into the myocardium, or placing it by air suction pads.

ii—Layer 2: is the layer that faces the inner cavity and functions through inflation and deflation causing contraction and relaxation thus propelling blood out of the heart in systole and accomodating a new blood volume in diastole.

i. Pneumatic (FIG. 4); by air, (driven by pump) or any other previously tested gas, causing inlation and deflation, an air mattress similar mechanism, or
  ii. Mechanically by contracting and relaxing fibers 'Concertina' (battery operated) vertically placed between two layers (FIG. 5) (through Piston, Magnet Drive, Piezoelectric crystal technology, . . . etc) or
  iii. Approximation of the facing walls can be operated by crossing bands of fibers (battery operated) fixed in opposing walls and crossing diagonally to the other side (FIG.6). One point working as origin and the other as insertion. (through Piston, Magnet drive, Piezoelectric crystal technology, . . . etc)

The material used to build the intra cardiac implant will be according to the latest researches; non-thrombogenic and non-antigenic; can be pericardial tissue enforced with patch, Poluurethane, PTFE, . . . etc.

Figure 4:
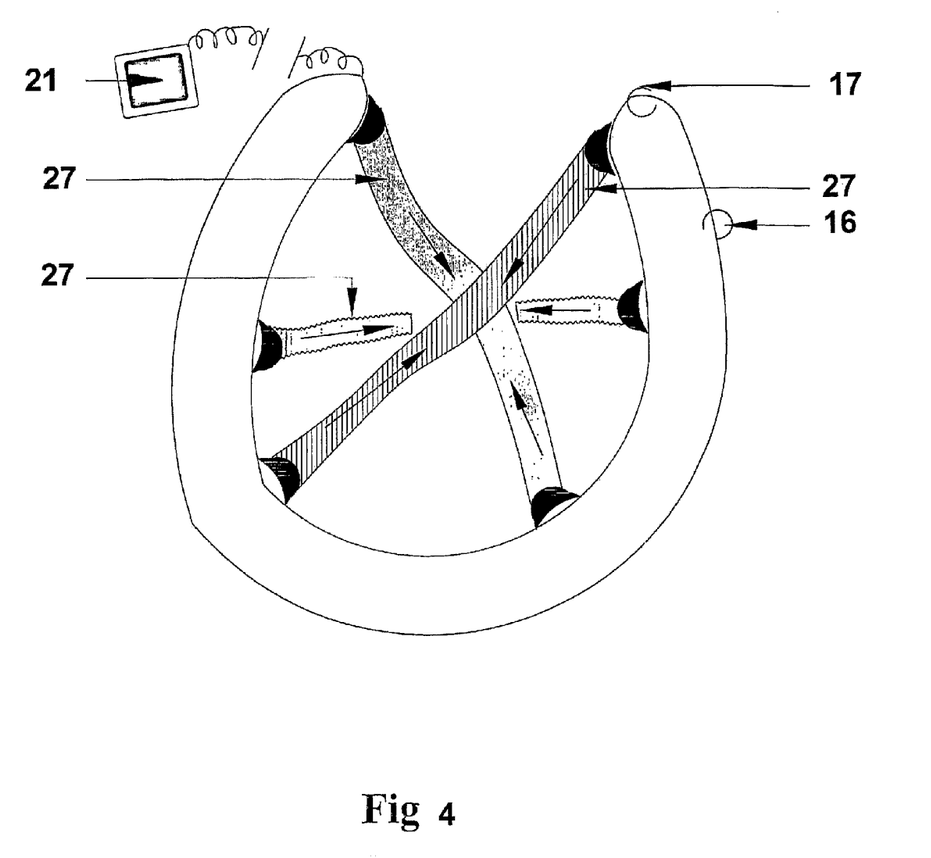
FIG. 4 is a perspective view of crossing diagonal bands of fibers.

FIG. 4 illustrates crossing diagonal band(s) of elastic fibers (27) from one point on layer 2 (17) to the facing point on an opposing elastic fiber (27). FIG. 4 illustrates the alternating polarity which allows traction (black arrows inside fibers show direction in systole). Diastole (not shown by the arrows inside the fibers) is caused by release in the opposite direction to systole. Elastic fibers (27) are attached to the surface of layer 2 (17) or from inside layer 2 (not shown). Finally the battery/programmer/pacer/DC shock/defibrillator (21) connects to the base of one or more fibers (27). Each elastic fiber or spring (22), contains several connected operating parts from inside. These parts are elastic element (reference numeral 33 in FIG. 8), electromagnetic coil (reference numeral 34 in FIG. 8), ferromagnetic core (reference numeral 35 in FIG. 8) and spring (reference numeral 36 in FIG. 8) shown and explained in FIG. 8.

Figure 5:
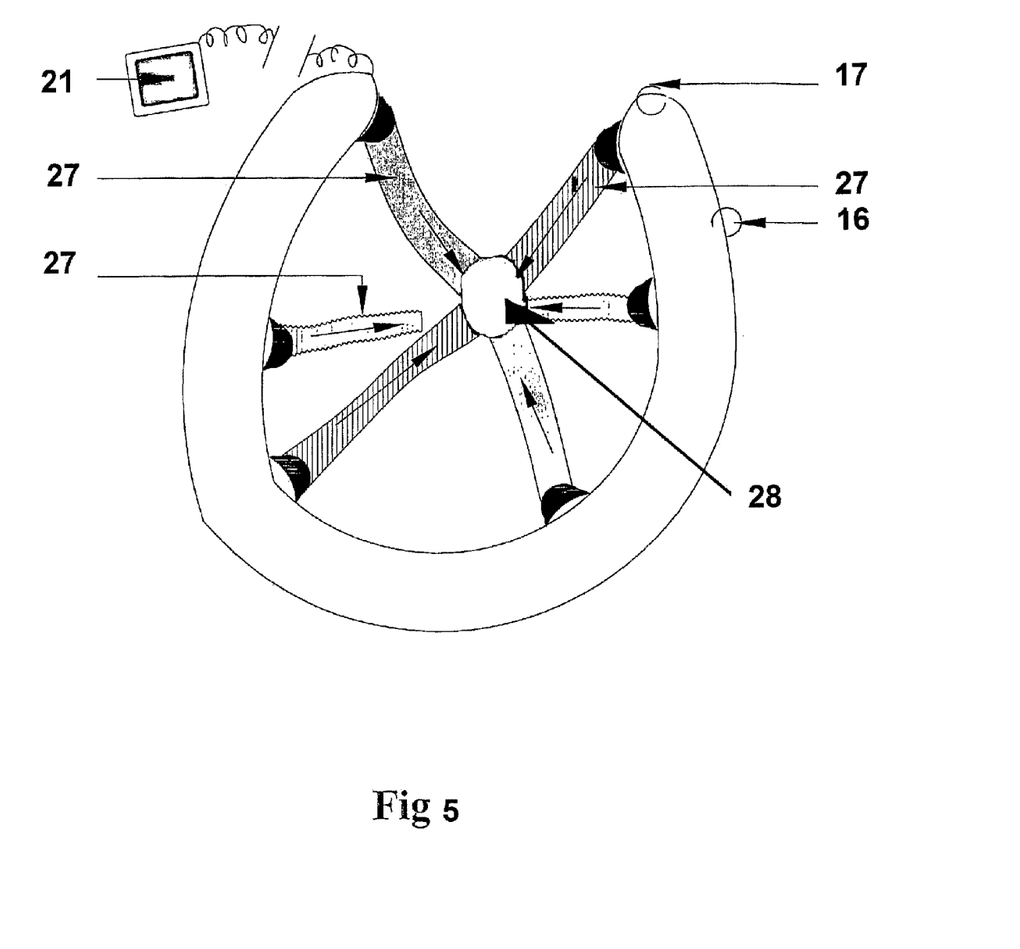
FIG. 5 is a perspective view of diagonal crossing intersecting band of elastic fibers of an exemplary embodiment of the present invention showing "SN"/"EMN".
Figure 6:
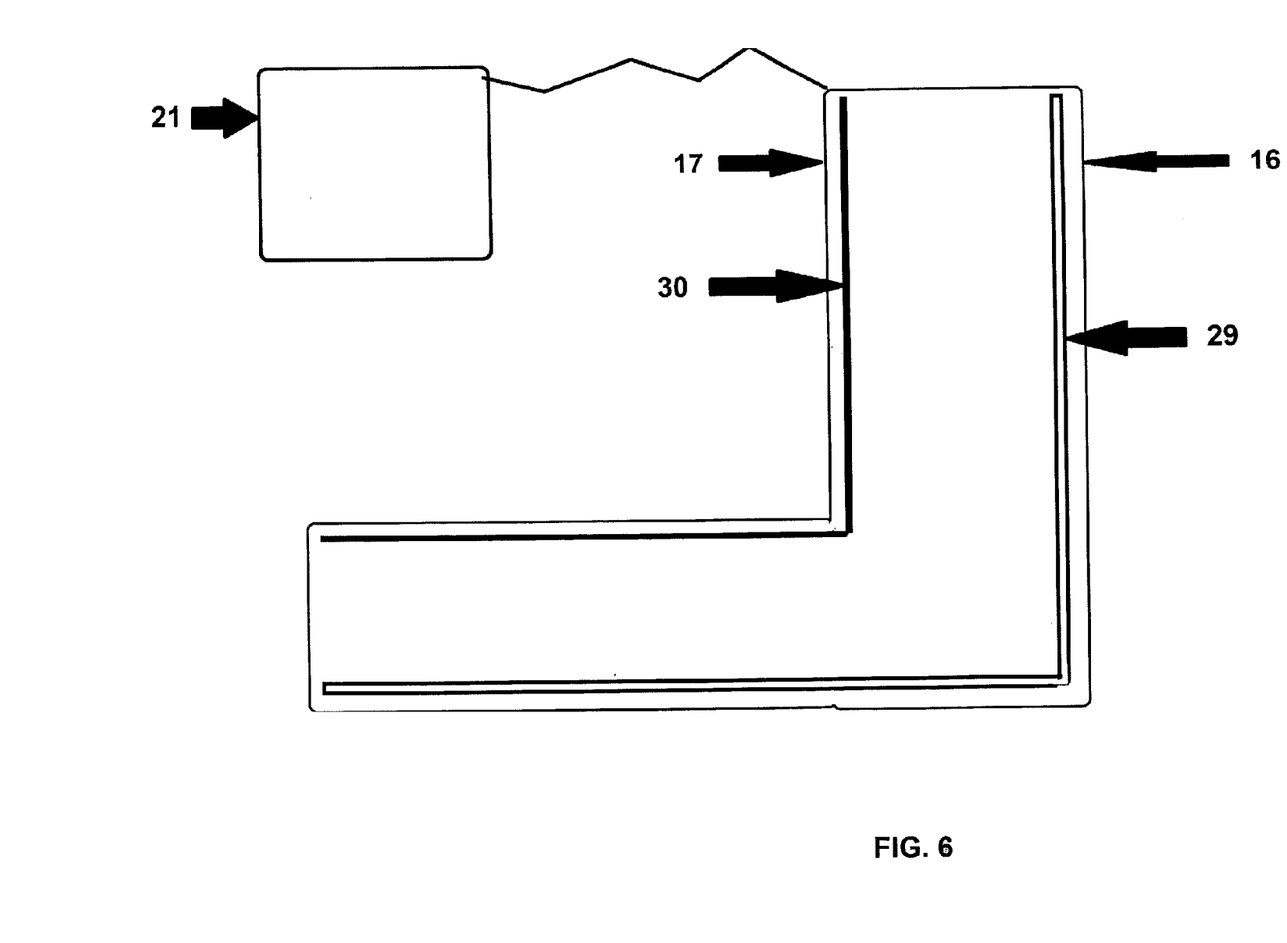
FIG. 6 is a perspective view of sheets with EM Coils that are adhered to both layers internally of the present invention.

Crossing diagonal band(s) of elastic fibers (27) from one point on layer 2 (17) to the opposite facing fiber is illustrated in FIG. 5. These fibers (27) meet and intersect at an electromagnetic node 'EMN' (28) or being a simple node 'SN' (28) serving only as a meeting point. This EMN (28) has a fixed polarity but with variable programmable magnitude. These fibers (27) are attached to the surface of layer 2 (17) or from inside layer 2 (not shown). Finally the battery/programmer/pacer/DC shock/defibrillator (21) connects to the base of one or more fibers (27). The electromagnetic variation delivered to these fibers changes their polarity. This results in their attraction to the EMN (28) 'systole' (black arrows inside fibers show direction in systole) representing systole. Repulsion from the EMN (28) 'diastole' (not shown by the arrows inside the fibers) is caused by release in the opposite direction to systole. A sheet (29) of EM coil(s) (as explained in the next figure) may be applied on the inner wall of layer 1 (16). This sheet contains EM coils (34) with polarities similar to that on layer 2 (17) attached fibers. The effect of this similar polarities is smoothing the return of layer 2 (17) in diastole so that it does not push layer 1 (16) further outside. During systole, this similar polarity will help push layer 2 (17) towards the cavity center. The magnitude of polarity of this sheet may be variable. The SN (28) functions as a point of intersection where all crossing fibers (27) meet. The SN (28) is a central station that allows crossing fibers (27) to shorten their limbs equally without having one limb shortening more pronounced than the other. As a result of the almost equidistant shortening and lengthening of each limb of each fiber (27), the corresponding layer 2 (17) is attracted and repelled to and from the center of the cavity. Each elastic fiber or spring (22), contains several connected operating parts from inside. These parts are elastic element (reference numeral 33 in FIG. 8), electromagnetic coil (reference numeral 34 in FIG. 8), ferromagnetic core (reference numeral 35 in FIG. 8), and spring (reference numeral 36 in FIG. 8) shown and explained in (FIG. 8).

FIG. 6 illustrates sheets with EM coils that are adherent to both layer 1 and layer 2. Layer 1 (16) of embodiment contains an internal sheet of material (29) composed of EM coils (reference numeral 34 in FIG. 8). Layer 2 (17) also holds another internal sheet (30) of EM coils (reference numeral 34 in FIG. 8) (as explained in FIG. 8). Both EM coils are set up facing each other. One sheet (29) has a fixed but variable programmable magnitude of EM coil polarity. The other sheet (30) has alternating EM coil polarity with variable magnitude as programmed. With both sheets (29 and 30) having the same EM coil polarity, one sheet (30), with its corresponding layer (17), is shifted away causing systole. When both sheets (29 and 30) have different EM coil polarities, the same sheet (30), with its corresponding layer (17), moves towards the other (16) causing diastole. Magnitude of electromagnetic field polarity determines the extent and distance, layer 2 (17) is moving. Electromagnetic field magnitude and direction is supplied through the battery/programmer/pacer/DC shock/defibrillator (21) which connects to the sheets (29 and 30) from inside. Each elastic fiber or spring (22), contains several connected operating parts from inside. These parts are elastic element (reference numeral 33 in FIG. 8), electromagnetic coil (reference numeral 34 in FIG. 8), ferromagnetic core (reference numeral 35 in FIG. 8) and spring (reference numeral 36 in FIG. 8) shown and explained in FIG. 8).

Figure 7:
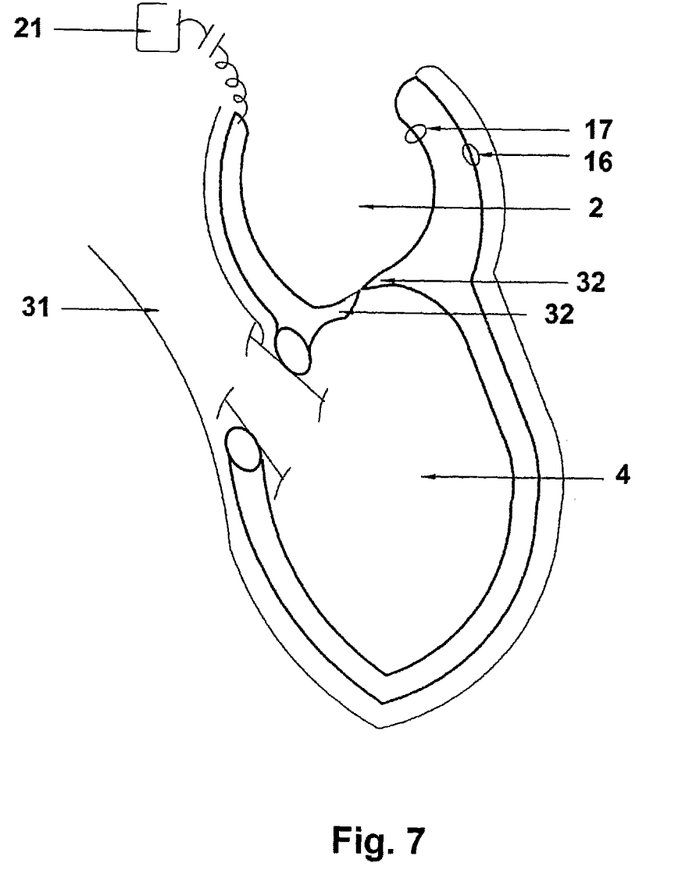
FIG. 7 is a perspective view of the operating parts that constrict at the level of the absent mitral valve to prevent mitral regurge in systole.

The operating parts constrict at the level of the absent mitral valve to prevent mitral regurge in systole, also known as MV surrogate. For example and as illustrated in FIG. 7, The embodiment layer 2 (17) has opposing walls at the level of the absent mitral valve (8), approximate with more inward protrusion towards the cavity center (32) in ventricular systole causing a constriction (32) that represents functional and positional mitral valve (8), also known as MV surrogate. This prevents the escape of blood in systole, from LV (4) into the LA (2) and permits full flow of blood into the aorta (31). Programming the constriction (32) is delivered through the embodiment connection to the battery/programmer/pacer/DC shock/defibrillator (21). In diastole, (not shown), the constriction (32) disappears.

Figure 8:
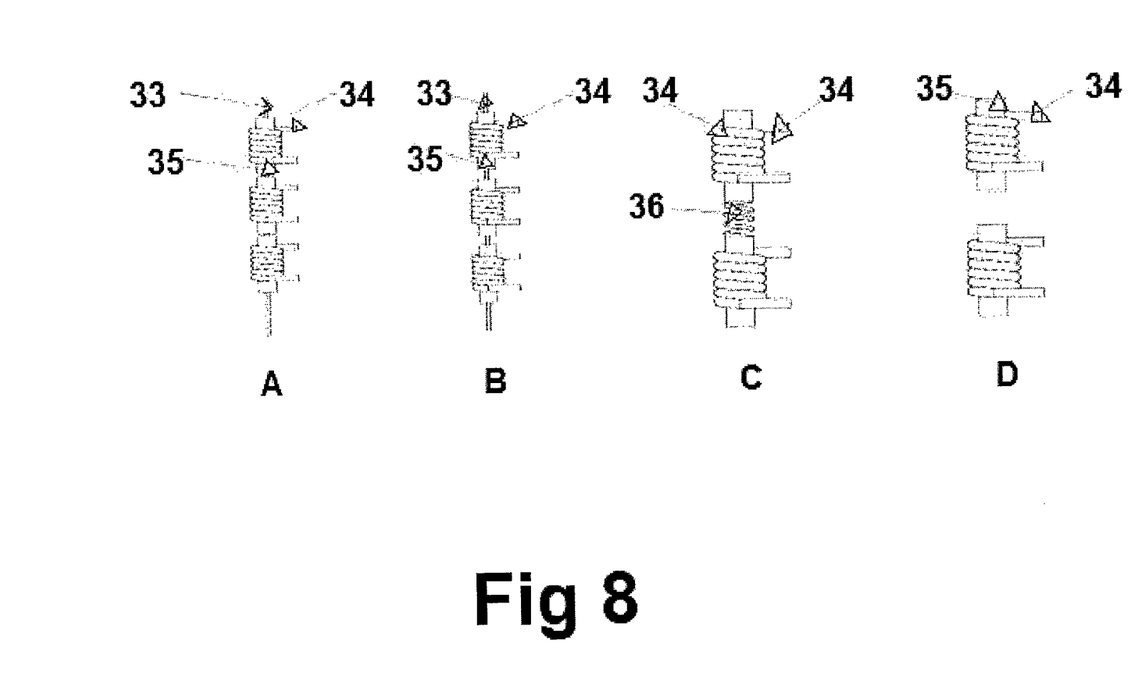
FIG. 8 is a perspective view of the electromagnetic system that operates the concertina elastic fibers and/or spring, the elastic crossing diagonal fibers, the elastic crossing diagonal intersecting fibers with EM node or SN node and sheets of EM coils.

In FIG. 8, A illustrates a diastole that is caused by electrical connection to the ferromagnetic part (35) and EM coil (34). Each elastic element (33) shortens by the effect of EM forces. Similar polarities repel and different polarities attract each other. This mechanism suits the crossing elastic fibers (reference numeral 27 in FIGS. 4 and 5) with (FIG. 5) or without (FIG. 4) the intersecting electromagnetic node (28) or the simple node (28). This is also suitable for the elastic fibers (reference numeral 22 in FIG. 3).

In FIG. 8, B illustrates systole that is caused by electrical connection to the ferromagnetic part (35) and EM coil (34). Each elastic element (33) lengthens by the effect of EM forces. Similar polarities repel and different polarities attract each other. This mechanism suits the crossing elastic fibers (27 in FIGS. 4&5) with (FIG. 5) or without (FIG. 4) the intersecting electromagnetic node (28) or the simple node (28). Also suits the elastic fibers (22 in FIG. 3).

In FIG. 8, C illustrates the mechanism of elastic fiber/spring (22 in FIG. 3) shortening and lengthening through the spring (36) between the 2 fibers. The movement starts with the electromagnetic application and depends upon the intensity of the current. The electric current direction is fixed, thus feeding the EM coils (34) at the 2 ends of the spring (36), each with a fixed but different polarity than its neighbor, i.e. one end is always 'North', the other end is always 'South'. Because this polarity is always different in the adjacent coils, the springs (36) and fibers (33) shorten (i.e. contract). The resultant shortening initiates and maintains diastole.

When one keeps the same electric current direction, (i.e. both ends of the spring (36) maintain their unlike polarities), but with less intensity, the spring (36) lengthens, initiating and maintaining systole. In the present application, the springing out of the fibers (33) or spring (36), need be stronger to face the high blood pressure, the polarity of one end of the spring (36) shifts between similar and dissimilar to the other. In such a case, when similar polarities exist between both ends of the spring (36) and fiber (33), repulsion occurs and systole is maneuvered. When both ends of the EM coils (34) are dissimilar, attraction occurs and diastole ensues. This mechanism also suits the elastic crossing fibers (reference numeral 27 in FIG. 4) and the elastic crossing intersecting fibers (reference numeral 27 in FIG. 5).

In FIG. 8, D the EM coils (34) illustrated show repulsion when their polarities are similar causing systole. They show attraction when their EM coils (34) are different, causing diastole. This mechanism suits the sheets of material (reference numerals 29 and 30 in FIG. 6).

All operations in the above mentioned applications depend upon the electric current connected to the electromagnetic coils (34). The functions and programmable parameters in the embodiment include:

Native Heart Rhythm (NHR) (with ICI embodiment): Sensing and tracking intrinsic "P" and "R" waves. Where a sensed event initiates a movement that augments the sensed signal. This fortifies systole and increases cardiac output (COP). In case, native signal is sensed, the embodiment functions as the ordinary pacemaker but in a continuous pacing mode.

Regular Implant Rhythm (RIR) Where no intrinsic electrical event, the embodiment fires a signal to drive the heart. This dominates until sensing of an event (with ICI) shifts the embodiment to the NHR once more. In such a condition, LV (4) filling will be reduced to only "Adequate Filling Phase" comprising the whole diastole. There will be no Rapid, Slow or Diastasis.

Defibrillation and DC shock delivery (with ICI) Upon sensing a supraventricular (RA/LA) or a ventricular (RV/LV) tachycardia or fibrillation, the embodiment attempts to terminate it by delivering a programmable number of DC/Defibrillation shocks. Once the attempt(s) succeed, the ICI embodiment drives the heart in NI-IR. Upon failure of reversion, the ICI embodiment ignores the dysrhythmia and switches to the RIR. There is no more immediate benefit from reverting to sinus rhythm. The ICI will function as a native heart muscle pump. More attempts of cardioversion may be delivered at a later programmable time that ranges from minutes to days.

The application of an ICI embodiment in one chamber and not the neighboring chamber mandates dysrhythmia termination in the free chamber. If a dysrhythmia emerges in a free chamber while its neighboring chamber casts an embodiment unit, one chamber will function properly and the other free chamber will function in dyssynchrony with its neighboring chamber. So this cadioversion illustrates the importance of dysrhythmia termination otherwise neighboring side-by side, chamber installation, of the embodiment is mandatory to guarantee inter chamber synchrony.

In case side-by side chambers hold an embodiment, ignoring the dysrhythmia (with ICI) is an advantage once cardioversion attempts have failed. In such a case all embodiment units will function as one electric and synchronous unit.

Restoration of normal AV valvar sequence Ventricular Systole; eg.; on left heart; will close the mitral valve (8) because the pressure in the LV (4) at this stage will be higher than the LA (2) pressure and this permits mitral valve closure. Diastole will open the mitral valve, because at this stage, the LA increasing pressure will force the mitral valve open. The embodiment will deliver an atrial kick (atrial systole) upon a programmed interval (similar to dual chamber pacers).

In case where the mitral valve (8) is absent, the embodiment itself will serve as a functional and anatomical mitral valve; MV surrogate. It protrudes more at the site of the absent mitral valve forming a constriction replacing the valve in systole. In diastole, the reverse occurs. The same applies to the right heart.

Correction of Dyskinesia, Intra-, and Interventricular dyssynchrony The embodiment application solves the problem of dyskinesis in wall motion due to controlled timing of systolic contraction and diastolic relaxation along the different sites.

This embodiment, unlike pacemakers which electrify the native heart muscle tissues, delivers its pacing to artificial tissue with artificial conducting system under programmable control. This function is not affected by the severity of native heart pathology. The systole/diastole; start, duration, rate, programmable response, amplitude of movement, force, function and sequence can thus be fully controlled in the desired segments of the embodiment. It can be programmed to mimic exactly the native healthy conduction; thanks to its network of fine cables embedded in-between the 2 layers (16 and 17).

In this way, there is total correction of intraventricular as well as interventricular dyssynchrony and SYNCHRONY can be restored between the various chambers, (i.e. Inter-, and Intrachambers Resynchronisation; Interatrial, interventricular, intraventricular and atrioventricular).

Exclusion of ventricular aneurysmal bulge, when covered with the "ICI" embodiment, will rid of its mechanical/electrical deleterious effects.

Diastolic function Diastolic dysfunction as well will be completely abolished and this term will be abandoned. With embodiment, the diastolic duration and extent can be manipulated as desired. The more retraction (relaxation) done by Layer 2 (17), the more the accommodated diastolic blood volume.

Optimizing venous return and cardiac output Through electrode (18) sensor(s) embedded in the walls of the atrial unit of the embodiment and connected to the battery circuitry, it can regulate the early and late diastolic ventricular filling.

During ventricular systole, blood volume and pressure in LA (2) are rising due to pulmonary venous drainage, lasting until the end of isovolumic relaxation phase. The sensor would now feel the weight and pressure of blood column in the LA and causes the MV barrage (native, artificial, or surrogate) to open. This opening will be maintained for a period of approximately a little >0.3 sec (the normal rapid ventricular and reduced ventricular filling) after which the atrial kick is delivered by the embodiment. The embodiment unit atrial kick starts by sensing the fall down in LA pressure during reduced ventricular diastasis that normally gives way to the native atrial systole.

What is claimed is:

1. A medical implant for placement in the interior of cardiac chamber having the same internal configuration and shape of the chamber and made of a non-thrombogenic and non-antigenic material comprising a magnet drive that causes electromagnetic movement of working parts of a first layer, and a second layer with each layer having an interior, whereby the working parts are selected from the group consisting of
    (a) an elastic fiber spring that is attached between the first layer and the second layer;
    (b) crossing intersecting bands of fibers on the second layer that meet and intersect at an electromagnetic node; and
    (c) sheets of electromagnetic material that attaches to the interior of both layers, a connecting system is embedded between the first layer and second layer, where the connecting system is composed of a battery/pacemaker/DC shock, fine cables and electrode sensors.

2. The medical implant according to claim 1, wherein the medical implant may be inserted in any one or more chambers, as a left side single unit (LA/LV) and/or a right side single unit (RA/RV).

3. The medical implant according to claim 1, wherein elastic fibers and/or a Spring System is vertically placed between the two layers spanning between the two layers or sitting on multiple layers (forming integrated force with less electromagnetic field dispersion into the surroundings).

4. The medical implant according to claim 1, wherein crossing intersecting bands of elastic fibers are disposed in/on the second layer, come out of the second layer and crossing diagonally to the opposing layer, wherein the fibers meet and intersect at an electromagnetic node.

5. The medical implant device according to claim 3, wherein the elastic fibers and a spring system are composed of a shielded elastic material capable of retracting and expanding that has a magnet drive.

6. The medical implant device according to claim 4, wherein the crossing intersecting bands of elastic fibers are composed of a shielded elastic material capable of retracting and expanding that has a magnet drive.

7. The medical implant device according to claim 1, wherein the electromagnetic node is composed of a shielded elastic material capable of retracting and expanding that has a magnet drive.

8. The medical implant device according to claim 1, further comprising signal and power booster stations disposed between the first layer and the second layer.

9. The medical implant device according to claim 1, further comprising a battery for providing power to a pacer programmer and DC shock to the medical implant device.

10. The medical implant device according to claim 6, wherein the battery is connected to at least one cable lead that serves as a single entry point into the body of the implant and not to a native heart tissue.

11. The medical implant device according to claim 7, further includes serial bridging cables.

12. The medical implant device according to claim 1, wherein the battery is internally charged by a thermocouple plate having a junction between two different metals and is implanted inside one or more cardiac chambers, body of implant or subcutaneously.

13. The medical implant device according to claim 1, wherein the battery is internally charged by a thermocouple plate having a junction between two different metals and is implanted inside one or more cardiac chambers, body of implant or subcutaneously.

14. The medical implant device according to claim 1, wherein the magnet drive has a ferromagnetic core and electromagnetic coil, and a spring.

15. The medical implant device according to claim 1, wherein an electromagnetic coil is shielded and insulated against electromagnetic leaks, and wherein a change in an electric current direction of field and intensity, causes a corresponding change in magnetic polarity and magnitude; with all similar polarities are repulsive and with all different polarities attractive.

16. The medical implant device according to claim 1, wherein an electromagnetic coil is shielded and insulated against electromagnetic leaks, and wherein a change in an electric current direction of field and intensity, causes a corresponding change in magnetic polarity and magnitude; with all similar polarities are repulsive and with all different polarities attractive.

17. The medical implant device according to claim 1, further comprising shielded sheets made of electromagnetic coils that are disposed on the first layer and the second layer from their interior surfaces facing each other, wherein the sheet is disposed on the first layer and has a fixed EM polarity and the sheet attached to the second layer has a changing EM coil polarity.

18. The medical implant device according to claim 1, further comprising an electromagnet node that is composed of a shielded elastic material capable of retracting and expanding that has a magnet drive.

\* \* \* \* \*